US012676212B2

(12) United States Patent　　　(10) Patent No.:　　US 12,676,212 B2
Langevin　　　　　　　　　　　　　　(45) Date of Patent:　　　　　Jul. 7, 2026

(54) SCAFFOLD CONTRAINED MOLECULAR GENERATION USING MEMORY NETWORKS

(71) Applicants:Sanofi, Paris (FR); Ecole Normale Supérieure, Paris (FR); Sorbonne Université, Paris (FR); Centre National de la Recherche Scientifique, Paris (FR)

(72) Inventor: Maxime Langevin, Paris (FR)

(73) Assignee: Sanofi, Paris (FR)

( * ) Notice: Subject to any disclaimer, the term of this patent is extended or adjusted under 35 U.S.C. 154(b) by 673 days.

(21) Appl. No.: 18/022,805

(22) PCT Filed: Aug. 25, 2021

(86) PCT No.: PCT/EP2021/073462
§ 371 (c)(1),
(2) Date: Feb. 23, 2023

(87) PCT Pub. No.: WO2022/043362
PCT Pub. Date: Mar. 3, 2022

(65) Prior Publication Data

US 2023/0420084 A1　　　Dec. 28, 2023

(30) Foreign Application Priority Data

Aug. 26, 2020　(EP) ..................................... 20315392

(51) Int. Cl.
*G16C 20/50*　　　(2019.01)
*G16C 20/70*　　　(2019.01)
(52) U.S. Cl.
CPC ............. *G16C 20/50* (2019.02); *G16C 20/70* (2019.02)

(58) Field of Classification Search
CPC ........ G16C 20/50; G16C 20/62; G16C 20/64; G16C 20/70
See application file for complete search history.

(56) References Cited

U.S. PATENT DOCUMENTS

| | | | | |
|---|---|---|---|---|
| 11,049,590 B1 * | 6/2021 | Lee | ........................... | G06N 3/08 |
| 2002/0156604 A1 * | 10/2002 | Rosenthal | .............. | G16C 20/60 |
| | | | | 703/2 |
| 2020/0168302 A1 * | 5/2020 | Isayev | ..................... | G16C 20/50 |
| 2021/0217487 A1 | 7/2021 | Xie et al. | | |

FOREIGN PATENT DOCUMENTS

| | | |
|---|---|---|
| CN | 110444250 A | 11/2019 |
| JP | 2020-009203 A | 1/2020 |
| WO | WO 2022/043362 | 3/2022 |

OTHER PUBLICATIONS

Olivecrona M, Blaschke T, Engkvist O, Chen H. Molecular de-novo design through deep reinforcement learning. J Cheminform. Sep. 4, 2017;9(1):48. doi: 10.1186/s13321-017-0235-x. PMID: 29086083; PMCID: PMC5583141. (Year: 2017).*

(Continued)

*Primary Examiner* — Yoshihisa Ishizuka
(74) *Attorney, Agent, or Firm* — Fish & Richardson P.C.

(57)　　　　ABSTRACT
A computer-implemented method of generating a molecule includes sequentially processing, by a memory network, each token in a token string representation of a molecular scaffold to generate a molecule, wherein the token string representation comprises a plurality of tokens representing predefined structures of the molecular scaffold and one or more tokens representing open positions of the molecular scaffold, and wherein the memory network encodes a sequential probability distribution on the tokens using an internal state of the memory network. The method further includes outputting, from the memory network, a token string representation of the generated molecule. Sequentially processing each token in the token string representation of (Continued)

the molecular scaffold includes determining whether or not a current token being processed is a token representing an open position of the molecule.

20 Claims, 5 Drawing Sheets

(56) References Cited

OTHER PUBLICATIONS

Arus-Pous et al., "SMILES-based deep generative scaffold decorator for de-novo drug design," Journal of Cheminformatics, May 29, 2020, 12(1):38.

Gupta et al., "Generative Recurrent Networks for De Novo Drug Design," Molecular Informatics, Jan. 1, 2018, 37(1-2):1700111.

International Preliminary Report on Patentability in International Appln. No. PCT/EP2021/073462, mailed on Mar. 9, 2023, 9 pages.

International Search Report and Written Opinion in International Appln. No. PCT/EP2021/073462, mailed on Nov. 26, 2021, 10 pages.

Langevin et al., "Scaffold-constrained molecular generation," arXiv. org, Oct. 5, 2020, 39 pages.

Popova et al., "Deep Reinforcement Learning for De-Novo Drug Design," arXiv.org, Nov. 29, 2017, 26 pages.

Weininger, "SMILES—A language for Molecules and Reactions," Handbook of Chemoinformatics: From Data to Knowledge, Gasteiger (ed.), Aug. 8, 2003, pp. 80-102.

* cited by examiner

500

504
Volatile memory

502
Processor apparatus

506
Non-volatile memory

SCAFFOLD CONTRAINED MOLECULAR GENERATION USING MEMORY NETWORKS

CROSS REFERENCE TO RELATED APPLICATIONS

The present application is the national stage entry of International Patent Application No. PCT/EP2021/073462, filed on Aug. 25, 2021, and claims priority to Application No. EP 20315392.9, filed on Aug. 26, 2020, the disclosures of which are incorporated herein by reference.

TECHNICAL FIELD

This specification relates to systems and methods for generating potential medicinal molecules under scaffold constraints using memory networks.

BACKGROUND

Finding new drugs is a long, costly and difficult problem, with potential failure all along the drug discovery pipeline and an overall success rate close to only 4%. Lead-optimization, where medicinal chemists refine bioactive molecules into potential drugs, takes a major part of the time and cost in the discovery pipeline. Finding a good drug candidate requires finding a molecule that is active on the target of interest while satisfying multiple criteria, such as those related to safety and ADME (Absorption, Distribution, Metabolism, Excretion). In this respect, lead-optimization can be viewed as a multi-objective optimization problem in chemical space.

There has been a recent surge of interest in generative models for de-novo drug design and their application in the drug discovery pipeline. Generative models have been studied for two types of tasks: distribution learning and goal-oriented learning. Distribution learning aims at reproducing the distribution of a known dataset, in order to sample a large library of molecules similar to the initial dataset used to train the generative model. Goal-oriented learning, on the other hand, takes as input a scoring function and aims at finding the molecules with the highest scores. Applying generative models to lead optimization can actually be understood as a special case of goal-oriented learning, where the scoring function reflects the adequacy of the molecule to the different project objectives. Distribution learning benchmarks are also frequently used to assess whether a model has learnt to generate drug-like molecules, and will be a good starting point for goal-oriented learning.

SUMMARY

According to a first aspect of this specification, there is described a computer implemented method of generating a potentially biologically/medically active molecule, the method comprising: sequentially processing, by a memory network, each token in a token string representation of a molecular scaffold to generate a potential molecule, wherein the token string representation comprises a plurality of tokens representing predefined structures of the molecular scaffold and one or more tokens representing open positions of the molecular scaffold, and wherein the memory network encodes a sequential probability distribution on the tokens using an internal state of the memory network; and outputting, from the memory network, a token string representation of the generated molecule. Sequentially processing each token in the token string representation of the molecular scaffold comprises: determining if a current token being processed is a token representing an open position of the molecule. If the current token does not represent an open position of the molecular scaffold, reading the current token into the memory network and updating the internal state of the memory network based on the current token. If the current token does represent an open position of the molecular scaffold, sampling one or more candidate tokens for the open position based on a current internal state of the memory network until a termination condition is satisfied and updating the internal state of the memory network after each sampled token based on said sampled token.

The one or more tokens representing open positions may represent one or more different open position types, and wherein the termination condition for sampling at an open position and/or tokens available for sampling at an open position are dependent on the type of said open position.

The method may further comprise resuming sequential processing of the token string representation of the molecular scaffold after the termination condition for an open position is satisfied.

At least one of the tokens representing an open position of the molecular scaffold may represent an open branch of the molecular scaffold. A set of allowed tokens for the token string representation may comprise a branch-opening token and a branch-closing token. Sampling one or more candidate tokens at an open position representing an open branch of the molecular scaffold may comprise sampling candidate tokens until a number of sampled branch-closing tokens is equal to a number of branch-opening tokens in the candidate tokens. One or more tokens of the branch may be constrained and/or the branch may be constrained to be a linear fragment.

At least one of the tokens representing an open position of the molecular scaffold may represent an open linker within the molecular scaffold. Sampling one or more candidate tokens at an open position representing an open linker of the molecular scaffold may comprise: determining a threshold number of candidate tokens to be sampled based on a pre-defined probability distribution; and sampling candidate tokens until a number of sampled tokens reaches the threshold number of candidate tokens.

A set of allowed tokens for the token string representation may comprise a branch-opening token and a branch-closing token and/or one or more cycle opening and cycle closing tokens. Sampling one or more candidate tokens at an open position representing an open linker of the molecular scaffold may further comprise continuing to sample candidate tokens beyond the threshold number of sampled tokens until all branches are closed and all cycles are closed.

Sampling one or more candidate tokens at an open position may comprises sampling the candidate tokens from a predefined set of discrete token choices that is a proper subset of the available tokens.

The memory network may comprise a recurrent neural network. The memory network may comprise a set of learned parameters that have been determined by training the memory network on a training dataset comprising a plurality of token strings each representing known molecular structures.

The token string representation may be a SMILES representation. Alternatively, the token string representation comprises a 1-letter or 3-letter amino acid representation.

According to a further aspect of this specification, there is described a computer implemented method of lead optimisation comprising iteratively: generating one or more potential molecular structures with a given scaffold using any of the methods described herein; scoring each of the one or more potential molecular structures using a scoring function representing one or more target properties of a molecule; storing potential molecular structures as part of a set of potentially biologically/medically active molecules if a threshold condition relating to the scoring function is satisfied; and fine tuning parameters of the memory network based on the score for each of the one or more potential molecular structures.

According to a further aspect of this specification, there is described a method of synthesising a potential biologically/medically active molecule, the method comprising: generating a structure of a potential biologically/medically active molecule using any of the computer implemented methods described herein; and synthesising the potential biologically/medically active molecule based on the generated structure.

According to a further aspect of this specification, there is described a computer program product comprising computer readable code that, when executed by a computing device, causes the computing device to perform any of the computer implemented methods described herein.

According to a further aspect of this specification, there is described a system comprising one or more processors and a memory, the memory comprising computer readable instructions that, when executed by the one or more processors, causes the system to perform any of the computer implemented methods described herein.

According to a further aspect of this specification, there is provided a drug comprising at least one biologically/medically active molecule generated using any of the methods described herein.

According to a further aspect of this specification, there is provided a drug comprising at least one biologically/medically active molecule synthesised using any of the methods described herein.

BRIEF DESCRIPTION OF THE FIGURES

Embodiments will now be described by way of non-limiting examples with reference to the accompanying drawings, in which:

FIG. 5 shows a schematic overview of an example system for performing any of the methods disclosed herein.

DETAILED DESCRIPTION

Real life lead optimization projects often impose constraints on the scaffold of designed molecules. Interesting scaffolds are identified during the lead identification phase of the pipeline, and often kept throughout the rest of the pipeline, with only minor changes or variations. The scaffold, or "core" of a molecule, is key to: (i) preserving biological activity identified earlier in the pipeline; (ii) staying within areas of chemical space where prior information gathered is relevant, making SAR (structure-activity relationship) understandable; and (iii) maintaining a high throughput for compound synthesis by using common precursors, speeding the Design-Make-Test-Analysis (DMTA) cycle to a level acceptable by industry standards. Therefore, lead-optimization can be thought of as a multi-objective optimization problem under scaffold constraints.

The systems and methods disclosed herein sample from a sequential probability distribution over tokens representing a molecular structure, while still accommodating scaffold constraints on the molecules, by understanding which tokens are allowed to be sampled at each step in the sequence of tokens. Furthermore, the systems and methods can resume reading a scaffold after sampling an open position, determining when to resume reading the scaffold as a function of the open position and previously sampled tokens for this open position.

Furthermore, scaffold-specific training is not required and only the sampling phase of an optimisation process needs to be modified. Doing so, a generic probability distribution on token strings describing a large and diverse corpus of drug-like molecules can be used to sample molecules with a specific scaffold. Thus, the same model can be used for various scaffolds, and retraining of the model for every new scaffold is not required.

Figure 1:
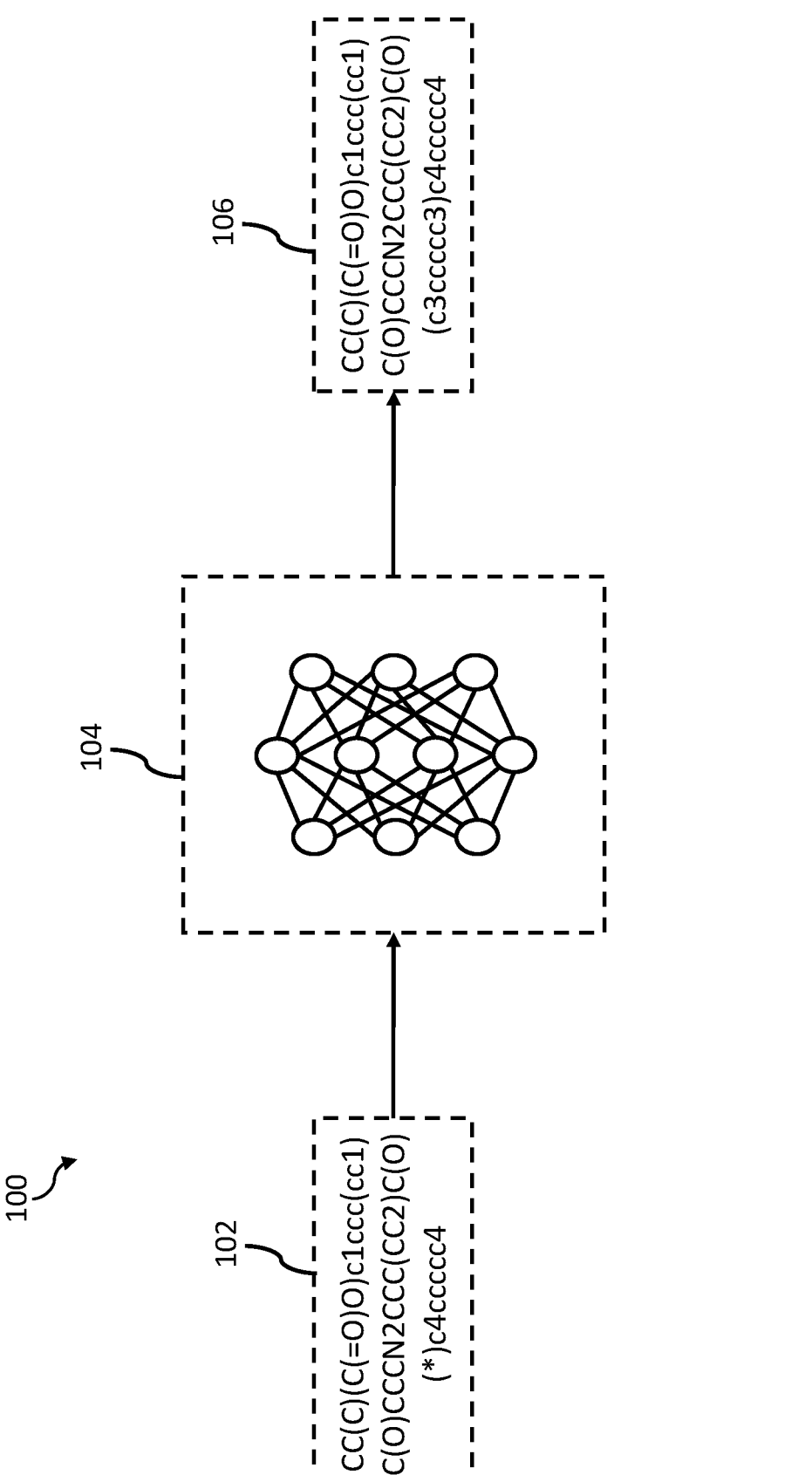
FIG. 1 shows a schematic overview of an example method of generating a molecular structure under scaffold constraints.

Also, the proposed method can complete multiple open positions at once/in one pass through the sequence of tokens. Moreover, the model expresses a joint probability distribution on the completions of the multiple open positions. This allows joint optimization of multiple open positions at the same time, which is not possible using existing methods FIG. 1 shows a schematic overview of an example method 100 of generating a molecular structure under scaffold constraints. The method may be performed by one or more computing systems operating in one or more locations.

A predefined molecular scaffold 102 is represented as a token string, s, (also referred to herein as a "character string") containing structural information about the molecular scaffold that comprises the predefined molecular structure of the scaffold and one or more "open" positions. The token string representing the molecular scaffold 102 is sequentially input into a memory network 104, which processes the input tokens sequentially to generate a complete molecular structure 106 of a potential molecule, which may be represented as a complete token string, $\{x_0, \ldots, x_n\}$, i.e. a token string containing no open positions. For scaffold constrained generation, the memory network 104 is constrained to follow the tokens of the token string representing the scaffold 102, with sampling enabled only when an open position of the molecular scaffold 102 is reached.

The token string representing the molecular scaffold 102 comprises string of tokens (also referred to as "characters"). The string of tokens comprises a plurality of "fixed" tokens that each correspond to an atom, structure or denote other structural information, such as opening or closing of cycles (e.g. by use of numbers) and branches (e.g. by use of parentheses), stereochemistry or multiple bonds (e.g. by use of the symbol "=" for a double bond, etc.). The tokens may, for example, include the atomic symbols of atoms. The tokens may further comprise tokens representing the opening and closing of branches of the molecule, e.g. opening and closing parenthesis to represent the start and end of a branch respectively. The tokens may comprise tokens representing molecular building blocks, such as amino acids, peptides or other multi-atom structures.

The token string representing the molecular scaffold 102 further comprises one or more "open" tokens that represent open positions in the scaffold at which additional molecular structures can be sampled. For example, each instance of the token "*" may represent an open position in the molecular scaffold. In other words, the token string representing the scaffold is an incomplete token string of a whole molecule. In some embodiments, the open positions may be divided in a plurality of sub-types. The subtypes may comprise one or more of: branching points, which provide branched decorations to the scaffold 102 (these may also be referred to as "R-groups", and may be denoted in the character string as "(*)"), linkers, that link different cycles of the molecule; and/or constrained choices, in which the possible tokens that can be sampled at the open position are limited to a proper subset of the available tokens. It should be noted that constrained choice-type open positions may be combined with branching points and/or linkers to create open positions comprising constrained branching points and/or constrained linkers.

In some embodiments, the token string 102 comprises an initialisation token that indicates the start of the token string 102. The token string may further comprise an end-of-string token indicating the end of the token string 102

An example of such a character string representation is the SMILES language (see, for example, "SMILES— A Language for Molecules and Reactions", Weininger D., Handbook of Chemoinformatics 2008, 80-102). To generate a SMILES representation of a molecule from a molecular graph, cycles are broken down and marked with numbers, and a starting atom is chosen. A SMILES string is obtained by printing the symbol of the nodes encountered in a depth-first traversal starting at the chosen atom, with parentheses indicating branching points in the graph. For a given molecular graph, there are as many SMILES as possible starting atoms. A canonicalization algorithm can be used to pick the starting atom (ibid.), thus yielding the canonical SMILES of the molecule. A corresponding molecular graph can be easily retrieved from a given SMILES.

The memory network 104 is a machine learned model that sequentially processes input tokens based on an internal state, h, of the memory network 104 (also referred to herein as a "hidden state"). The internal state is updated after the processing of each token in the sequence of input tokens based on learned parameters of the memory network, e. The internal state of the memory network 104 stores information about the tokens processed so far by the network 104. Processing an input token comprises reading the token into the memory network 104 and generating one or more corresponding output tokens. Depending on the input token, the output token may just be the input token, e.g. if the input token is fixed token, then the corresponding output is the fixed token. If the input token corresponds to an open token, then the memory network 104 generates one or more output tokens by sampling possible tokens based on a current state of the memory network. In either case, the state of the memory network 104 is updated following the processing of the input token.

The memory network may be a memory neural network. An example of such a network is a Recurrent Neural Network (RNN), such as a Long-Short-Term Memory (LSTM) network.

The memory network 104 can generate an output token string representing a molecule 106 in a sequential fashion by modelling a conditional probability distribution over characters/tokens of the string, conditioned on the characters in the string so far. The memory network 104 relies on its internal state h to process the information from the previous tokens, $\{x_0, \ldots, x_{t-1}\}$ and generate the next output token $x_t$, and models the conditional probability $P(x_t|x_0, \ldots, x_{t-1})$ as $P(x_t|h_{t-1})$, i.e. the conditional probability is encoded using the hidden state. The process may, in some embodiments, be represented by the following algorithm:

---

Algorithm 1: Generating a molecular token string with scaffold constraints

| | |
|---|---|
| Result: | Molecular token string with scaffold s |
| Input: | scaffold $s = s_1, \ldots, s_n$ |
| initialise | $h_0$ ; |
| | $x_0$=GO ; |
| | t=1 ; | for i ← 1 to n do
│    if $s_i$ not * then
│    │    Read $s_i$ and update $h_{t-1}$ to $h_t$ ;
│    │    $x_t = s_i$ ;
│    │    t = t+1 ;
│    else
│    │    Sample $y = (y_1, \ldots, y_k)$ and update h according to sampling
│    │    procedure ;
│    │    $x_t, \ldots, x_{t+k} = y_1, \ldots, y_k$ ;
│    │    t = t+k ;
end
t= t+1 ;
$x_t$ = EOS ;
Output: $x_0, \ldots, x_t$

---

Here, GO and EOS are the initial and final tokens of the string respectively, and y is a length k string of sampled tokens, $y_1, \ldots, y_k$. The sampling procedure may be dependent on the type of open position being sampled.

Sampling at the open position continues until a termination condition is satisfied. Once the termination condition is satisfied, the memory network resumes reading the next token in the input token string representation (i.e. the scaffold).

The termination condition for the open position may depend on a type of the open position (e.g. whether it is a branching point, a linker position or some other type of open position). The termination condition may alternatively or additionally be dependent on the tokens sampled so far.

In some embodiments, if the open position is a branching point, the memory network 104 samples tokens as long as the branch is open. When a branch-closing token matching the branch-opening token is sampled, the branch is finished, and the memory network 104 resumes reading the rest of the scaffold 102. In some embodiments, during sampling the memory network 104 may sample additional branch-opening tokens (e.g. an open parenthesis "("). In these embodiments, an additional branch-closing token (e.g. a closing parenthesis ")") should be sampled before the overall branch is closed. The overall opening and closing of parentheses is therefore tracked during the sampling. The sampling may be ended when the number of branch-closing tokens becomes equal to the number of branch-opening tokens.

The sampling procedure for a branching point may be given by the following example algorithm:

---

Algorithm 2: Decorating a scaffold on a given branching position

| | |
|---|---|
| Result: | Token string for completed branch ("decoration") |
| Input: | hidden state h |
| initialise | $h'_0 = h$ ; |
| | opened = 1 ; |
| | closed = 0 ; |

-continued

| Algorithm 2: Decorating a scaffold on a given branching position |
|---|

```
while opened > closed do
        Sample x_t from P(x | h'_{t-1}) and update h'_{t-1} to h'_t ;
        if x = branch-opening token then
        |       opened += 1 ;
        else if x = branch-closing token then
        |
                closed += 1 ;
        t= t+1 ;
end
```

In some embodiments, additional constraints may be placed on the sampling procedure for the branch. For example, the initial tokens of the branch may be specified (e.g. "(CN*)" instead of "(*)"), and/or the branch may be constrained to be a linear fragment by forbidding the opening of new branches/cycles (e.g. by preventing sampling of branch-opening and branch-closing tokens).

If the open position is a linker (e.g. a linker between cycles), there will be no indication of when to finish the sampling, in contrast to the branching position case. Instead, for a linker position, a pre-defined probability distribution for the length of the sample/fragment, $P_{size}$, is used to determine when to end the sampling. The pre-defined probability distribution for the length of the sample/fragment may be user-defined. The ability to modify the core of a molecule using linker open positions allows the method to tackle more than simple scaffold decoration, and thus perform e.g. scaffold hopping as well.

The pre-defined probability distribution can be used to define a number of tokens/characters, $n_{char}$, to be sampled.

In some embodiments, one or more of the linker open positions may be constrained to have no branches and/or cycles (e.g. forbidden for sampling branch-opening and branch-closing tokens). In these embodiments, the pre-defined probability distribution for the length of the sample/fragment is used to determine when to stop sampling for the linker open position.

In some embodiments, the one or more of the linker open positions may be allowed to generate additional branches and/or cycles during sampling (e.g. sample branch-opening and branch-closing tokens). For these linker open positions, the branch-opening and branch-closing tokens are tracked to ensure that branches and cycles are completed before sampling is finished, i.e. that the fragment/sample contains no open cycles and/or open branches. The stopping criteria for such linker open positions is thus a combination of the pre-determined probability distribution and a condition that the fragment/sample contains no open cycles and/or open branches.

The sampling procedure for a linker point may be given by the following example algorithm:

| Algorithm 3: Scaffold hopping by linker completion |
|---|

```
Input:      hidden state h, pre-defined distribution on linker size, P_{size}
Result:     Token string with completed linker
initialise  h'_0 = h ;
            sample n_{char} from P_{size}
            opened = 0 ;
            closed = 0 ;
            cycle = False ;
```

-continued

| Algorithm 3: Scaffold hopping by linker completion |
|---|

```
while cycle or step <n_{char} or opened > closed do
|       Sample x_t from P(x | h'_{t-1}) and update h'_{t-1} to h'_t ;
|       if x = branch-opening token then
|       |       opened += 1 ;
|       else if x = branch-closing token then
|       |       closed += 1 ;
|       else if x_t = {1, 2, ... , 9} then
|       |       if corresponding cycle not opened then
|       |       |       cycle = True ;
|       |       |       keep track of corresponding cycle ;
|       |       else
|       |       |       close corresponding cycle ;
|       if no cycle still opened then
|       | cycle = False ;
        step = step + 1 ;
end
```

In some embodiments, the sequences of tokens available for sampling at an open position may be restricted to a pre-defined number of discrete choices, i.e. a proper subset of the possible token strings that could be sampled at the open position. During lead optimization campaigns, small variations on the scaffold are often encountered, and hence it may be beneficial to restrain the choices to the few possibilities that exist in this given context.

To implement this, the language used for the token string representation may be extended to deal with such discrete choices. An example of such an extension is the SMARTS language, an extension of SMILES, that deals with discrete choices. In this example, a discrete choice between k characters/sequences may be represented as $[x_1; x_2; \ldots ; x_k]$. This syntax may be used for sampling between a finite set of discrete choices. Sampling procedure may be achieved by restricting the possible sampled tokens to those present in the discrete choices. The probability distribution may be renormalized and then sampled. In some examples, instead of drawing the next token from $P(x_t|h_{t-1})$, it may be sampled from:

$$Q(x) = \text{softmax}\left[ P(x|h_t) \cdot \sum_{c \in choices} \delta x, c \right]$$

Reinforcement Learning (RL) can be applied to the method 100 to design optimized molecules either through policy gradient or hill-climbing, which both aim at maximizing the probability of the highest scoring token strings by fine tuning the memory network to generate high scoring molecules. Hill-climbing has been shown to achieve state-of-the-art results on various goal-oriented benchmarks. Examples of reinforcement learning techniques are described below in further detail in relation to FIG. 3.

The method can complete multiple open positions at once (e.g. in one pass through the token sequence). Moreover, the memory network expresses a joint probability distribution on the completions of the multiple open positions. This can allow joint optimization of multiple open positions at the same time using the RL methods described herein, which is not possible using existing methods.

Figure 2:
FIG. 2 shows a schematic overview of an example method of training a memory network to generate a molecular structure.

FIG. 2 shows an overview of a method 200 of training a memory network. The method may be performed by one or more computing systems operating in one or more locations.

During training, the memory network 204 receives an initial input 202 and generates a token string representing a molecule 206. An objective function 208 (also referred to herein as a "loss function") is used to determine parameter updates to the memory network 206 based on the output token string 206.

The input 202 may, for example, be a start-of-string token. The input 202 may alternatively be a token string representing a known start to a molecule in the training dataset.

The memory network 204 generate output token strings 206 in a sequential fashion by modelling the conditional probability distribution over tokens, conditioned on the beginning of a token string, i.e. the token string so far in the memory network 204. Let $s = x_0, \ldots, x_n$ the tokenized version of a molecular string, with $\{x_i\}$ being tokens/characters from a language, such as SMILES. In some embodiments, $x_0$ and $x_t$ denote respectively start-of-string and end-of-string tokens. The memory network 204 models $P(x_t | x_0, \ldots, x_{t-1})$, i.e. the conditional probability of a token given the previous tokens in the string.

The memory network 204 is trained on a training dataset of drug-like molecules to predict a next token given the beginning of the sequence. The molecules in the training dataset may be taken from a database of drug-like molecules. An example of such a database is ChEMBL20, though it will be appreciated that other databases may alternatively be used. The drug-like molecules are represented as a token string in the database or converted to one before input into the memory network 202. A validation dataset, used to validate the memory network 204, may also be generated from a database of drug-like molecules. This database may be a subset of the database of drug-like molecules.

The training dataset may be a generic dataset, comprising diverse drug-like compounds. A memory network 204 trained on such a dataset may be able to explore a large and varied chemical space when generating potentially interesting molecules.

Alternatively, the training dataset may be a focused training dataset, comprising molecules from one or more predefined chemical series (e.g. a single chemical series). A memory network 204 trained on such a dataset may be able to generate close analogues to a given chemical series.

As an example, the training dataset may be generated from the database by extracting a predefined number (e.g. 1.2 million) of molecules from the database (e.g. ChEMBL) and filtering them using one or more pre-defined criteria. The predefined criteria may comprise one or more of: size; atoms present; and/or presence/absence of macrocycles.

To validate the ability to generate molecules around new scaffolds, a validation dataset may be generated. The validation dataset may be generated from a known database of molecules, such as the SureChEMBL23 database, a database of patented molecules. Molecules may be clustered by their Bemis-Murcko scaffold, and a predefine number (e.g. 18) of chemical series may be extracted with different scaffolds. These scaffolds may be chosen for validation based on being sampled from real life drug discovery projects and not being present in the training set. Alternatively or additionally, any molecule that has one of these scaffolds may be removed from the training set.

To explore a focused region of chemical space and design analogues to a given series, the largest molecules (e.g. largest 93 molecules) may be isolated from among the extracted chemical series. This yields a number of scaffolds (e.g. 17) for the validation set, and one scaffold for a focused learning validation set.

Training is achieved by iteratively applying an optimisation procedure to a loss function 208, L, in order to determine updates to parameters of the memory network 204, $\theta$. The objective of the optimisation procedure may be to minimize the loss function 208 with respect to the memory network 204 parameters. The optimisation procedure may, for example, be a gradient descent method, such as stochastic gradient descent. The loss function may be a negative log-likelihood of the training set token strings, for example:

$$L(\theta) = -\sum_{t=1}^{T} \log P(x_t | x_0, \ldots, x_{t-1})$$

where $x_0$ is the initial token of the token string, and the token string has a total length of T tokens. The memory network 204 uses its current internal state, h, to process the information from the previous tokens, and models the conditional probability $P(x_t | x_0, \ldots, x_{t-1})$ as $P(x_t | h_{t-1})$. The internal state of the memory network 204 at step t, $h_t$, is dependent on the tokens in the string so far, $x_0, \ldots x_t$, and the parameters of the memory network, e.

In some embodiments, the training dataset is augmented by enriching the training dataset with non-canonical token strings. This can improve the performance of the memory network 204 once trained.

Once the conditional probability distribution $P(x_t | x_0, \ldots, x_{t-1})$ is learnt, sampling an entire token string may be achieved by initializing the sequence with a GO token, and then sampling tokens sequentially. This procedure ends when a end-of-string token is sampled, and returns a token string with its corresponding likelihood, which is amenable to backpropagation. However, the trained memory network may also be used for scaffold constrained generation, as described above in relation to FIG. 1.

Figure 3:
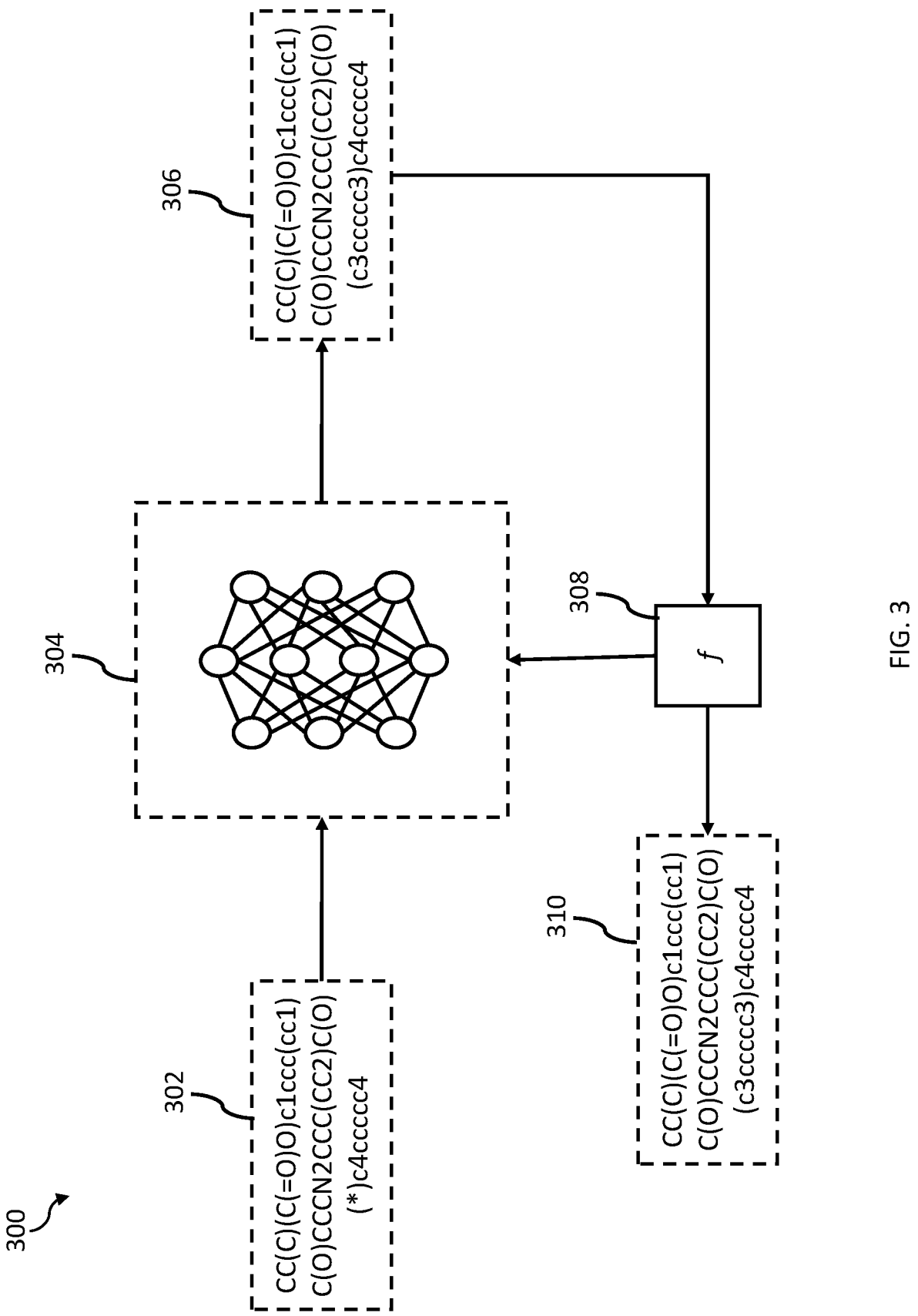
FIG. 3 shows a schematic overview of an example method of generating a molecular structure under scaffold constraints using reinforcement learning.

FIG. 3 shows a schematic overview of an example method 300 for generating potentially medically active molecules using a memory network. The method may be performed by one or more computing systems operating in one or more locations.

The method of FIG. 1 may be used as a sub-routine of a reinforcement learning method for generating potential biologically/medically active molecules. A memory network 304 is used to generate token strings representing potential molecules 306 from a pre-defined scaffold 302. The output token string representations 306 (or the molecules they represent) are scored using a scoring function 308 representing one or more target properties of a molecule. Parameters of the memory network 304, e, are fine-tuned based on scores for the generated molecules with the goal of, for example, maximising the score. Generated molecules satisfying a threshold condition based on the scoring function 308 are kept to generate a set of potentially biologically/medically active molecules 310.

The scoring function 308 may, for example, represent whether the molecule is likely to be active towards a biological target of interest. The scoring function 308 may be a mathematical function, and/or generated by performing one or more experiments on the molecules. The scoring function may be based on a predicted $pIC_{50}$ score of the molecule. As an example, the scoring function may be given by:

$$f = \max(1, 1 - (7.5 - pIC_{50})/7.5)$$

Another example of a scoring function is the QSAR model, though it will be appreciated that other functions can be used depending on the targeted properties.

The parameters, e, of the memory network 304 are fine-tuned based on this scoring function 308. For example, a hill climbing method or policy gradient method may be applied to the scoring function. This fine-tuning process may be iterated, with generated molecules having a score above a threshold value being kept, and molecules with a score below the threshold being discarded.

Alternatively, the top N molecules (e.g. 50) per iteration may be kept. A predefined number of reinforcement learning runs (e.g. 10) may be applied to generate the set of potentially medically active molecules 310.

In some embodiments, only the top scoring molecules (e.g. top 50) in the set of potentially medically active molecules 310 are kept, with the rest being discarded. These molecules may be synthesised to determine if they are indeed biologically/medically active.

Using a scaffold constrained method to generate molecules for the reinforcement learning method can improve a fraction of generated molecules that satisfy design requirements for the molecule. Furthermore, since the memory network encodes a joint probability distribution over the tokens, optimising the memory network using reinforcement learning can jointly optimise over multiple open positions at once.

Figure 4:
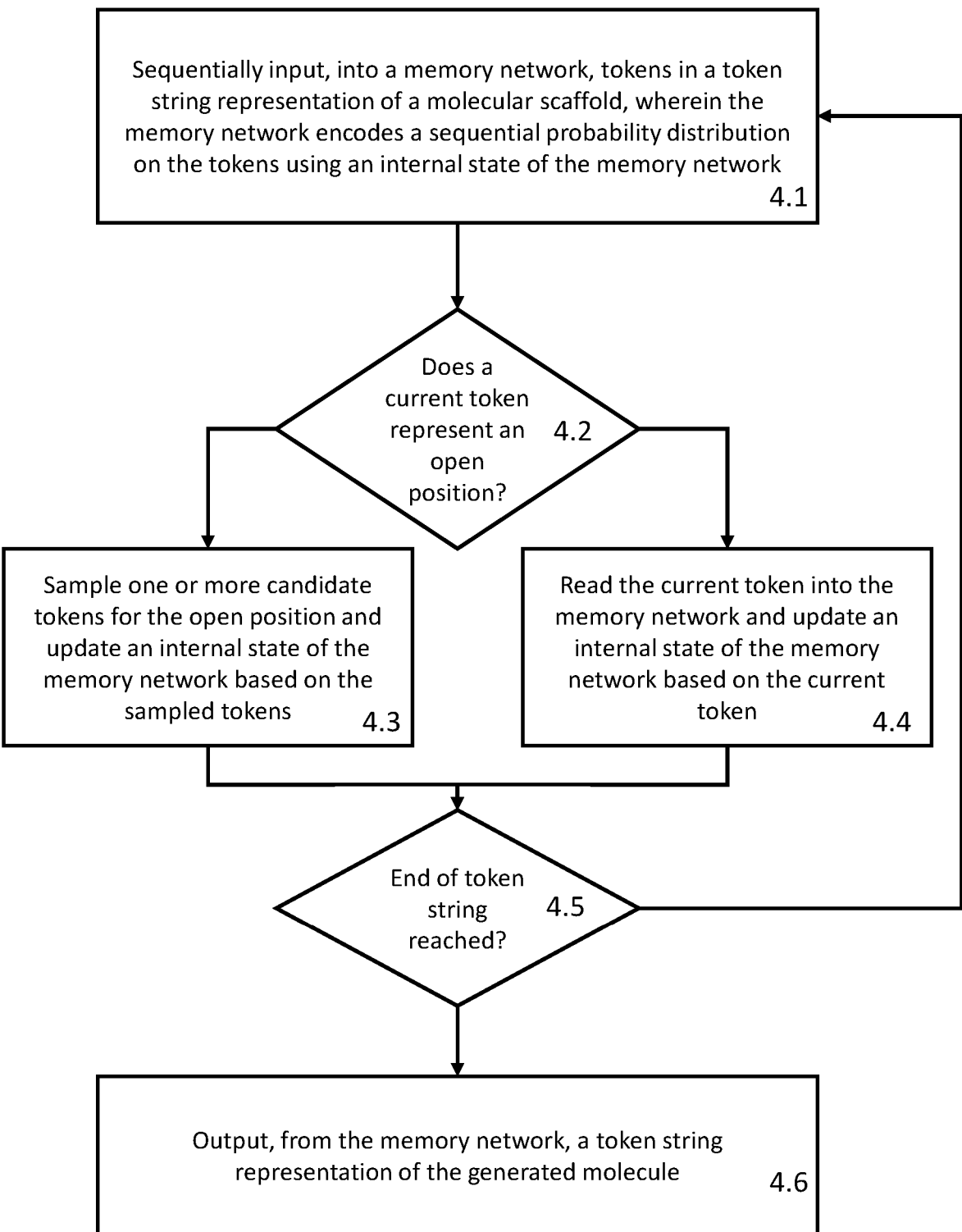
FIG. 4 shows a flow diagram of example method of generating a molecular structure under scaffold constraints.

FIG. 4 shows a flow diagram of an example method of generating a potential molecular structure under scaffold constraints. The method may be performed by one or more computing systems operating in one or more locations.

Tokens of a token string representing a molecular scaffold are sequentially input into a memory network, which processes them to generate a potential medicinal molecule.

At operation 4.1, a token from a token string representing a molecular scaffold is input into a memory network. This may be an initial token of the sting, or the next token in the string that has not yet been processed. This token is referred to as the "current token". The token string may be a SMILES representation. The memory network may be a recurrent neural network, such as a LSTM network. The memory network may comprise a set of learned parameters, that have been determined by training the memory network on a training dataset comprising a plurality of token strings each representing known molecular structures. The memory network encodes a sequential probability distribution on the tokens using an internal state of the memory network, h, as described above.

At operation 4.2, it is determined if the current token being processed represents an open position of the molecular scaffold. If it is determined that the current token represents an open position of the molecular scaffold, the method proceeds to operation 4.3. If it is determined that the current token does not represent an open position of the molecular scaffold (e.g. it represents a fixed structure/constraint of the molecular scaffold), the method proceeds to operation 4.4.

At operation 4.3, one or more candidate tokens for the open position are sampled based on the current internal state of the memory network, h, and the internal/hidden state of the memory network is updated based on the sampled tokens. Updating the hidden state of the memory network may further be based on learned parameters, e, of the memory network.

Tokens at the open position are sampled (and added to the token string) until a termination condition for the open position is satisfied to generate a token string for the open position comprising one or more tokens. The termination condition may be based on the type of open position currently being populated (e.g. an open branch or a linker position), and/or the tokens sampled so far. The method then proceeds to operation 4.5 (i.e. resumes reading the input token string).

The internal state of the memory network, h, may be updated for each of the sampled tokens. In other words, for every token that is sampled and added to the token string, the internal state of the memory network is updated based on the sampled token. When a plurality of tokens are sampled, the internal is thus updated a plurality of times.

In some embodiments, at least one of the tokens representing an open position of the molecular scaffold represents an open branch of the molecular scaffold, for example represented by the token "(*)".

The set of allowed tokens for the token string representation may comprise a branch-opening token and a branch-closing tokens. In these embodiments, sampling one or more candidate tokens at an open position representing an open branch of the molecular scaffold comprises sampling candidate tokens until a number of sampled branch-closing tokens is equal to a number of branch-opening tokens in the candidate tokens. This ensures that the branch (and its sub-branches) are properly closed.

The open branch may be unconstrained. The open branch may be constrained. For example, the open branch may be constrained to be a linear fragment (e.g. have no sub-branches and/or cycles) and/or to have pre-defined initial structure.

In some embodiments, at least one of the tokens representing an open position of the molecular scaffold represents an open linker within the molecular scaffold. In such embodiments, sampling one or more candidate tokens at an open position representing an open linker of the molecular scaffold may comprise: determining a threshold number of candidate tokens to be sampled based on a pre-defined (e.g. user defined) probability distribution; and sampling candidate tokens until a number of sampled tokens reaches the threshold number of candidate tokens.

The set of allowed tokens for the token string representation in such embodiments may comprise a branch-opening token and a branch-closing token (e.g. "(" and ")") and/or one or more cycle opening and cycle closing tokens (e.g. numbers). Sampling one or more candidate tokens at an open position representing an open linker of the molecular scaffold further may comprise continuing to sample candidate tokens beyond the threshold number of sampled tokens until all branches are closed and all cycles are closed.

A linker may be unconstrained. A linker may alternatively be constrained. For example, the linker may be constrained to be a linear fragment (e.g. have no branches and/or cycles) and/or to have pre-defined initial structure.

It should be noted that a scaffold may comprise both open branches and linkers.

Sampling one or more candidate tokens at an open position may comprise sampling the candidate tokens from a predefined set of discrete token choices that is a proper subset of the available tokens/token sequences.

At operation 4.4, the current token is read into the memory network and the internal state of the memory network, h, is updated based on the current token. Updating the hidden state of the memory network may further be based on learned parameters, θ, of the memory network. An output token of the generated molecule corresponding to such an input token is constrained to be that input token, i.e. no other tokens are sampled using the memory network. The method then proceeds to operation 4.5.

At operation 4.5, it is determined if the end of the token string has been reached. If an end-of-string token has not been reached, the method returns to operation 4.1 and the next token in the sequence is input into the memory network (or, alternatively, the generated molecule so-far is input into the memory network). If the end-of-string token has been reached, the method proceeds to operation 4.6.

In some embodiments, operation 4.5 may alternatively be performed prior to operation 4.2, with the method proceeding to operation 4.3 if the end token has not been reached and operation 4.6 if the end token has been reached.

At operation 4.6, the generated token string representation of the molecule is output by the memory network. The output molecules may be synthesised to determine if they are biologically/medically active.

It should be noted that this approach, described above using SMILES as the token string to represent molecules, could also be applied using other character/token string representations of molecules, such as single letter or three letter amino-acid codes for peptides and proteins. This allows for the generation of larger molecules under scaffold constraints.

Figure 5:
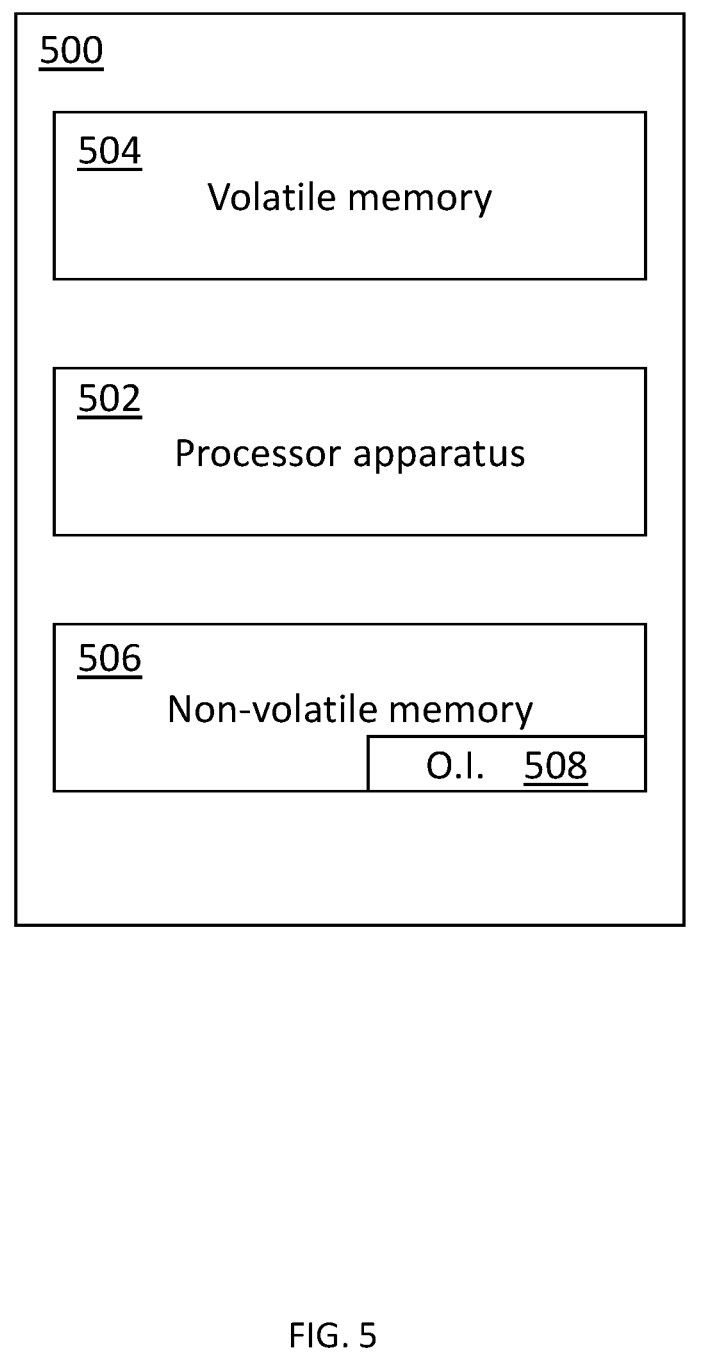

FIG. 5 shows a schematic example of a system/apparatus for performing any of the methods described herein. The system/apparatus shown is an example of a computing device. It will be appreciated by the skilled person that other types of computing devices/systems may alternatively be used to implement the methods described herein, such as a distributed computing system.

The apparatus (or system) 500 comprises one or more processors 502. The one or more processors control operation of other components of the system/apparatus 500. The one or more processors 502 may, for example, comprise a general-purpose processor. The one or more processors 502 may be a single core device or a multiple core device. The one or more processors 502 may comprise a Central Processing Unit (CPU) or a graphical processing unit (GPU). Alternatively, the one or more processors 502 may comprise specialised processing hardware, for instance a RISC processor or programmable hardware with embedded firmware. Multiple processors may be included.

The system/apparatus comprises a working or volatile memory 504. The one or more processors may access the volatile memory 504 in order to process data and may control the storage of data in memory. The volatile memory 504 may comprise RAM of any type, for example, Static RAM (SRAM), Dynamic RAM (DRAM), or it may comprise Flash memory, such as an SD-Card.

The system/apparatus comprises a non-volatile memory 506. The non-volatile memory 506 stores a set of operation instructions 808 for controlling the operation of the processors 502 in the form of computer readable instructions. The non-volatile memory 506 may be a memory of any kind such as a Read Only Memory (ROM), a Flash memory or a magnetic drive memory.

The one or more processors 502 are configured to execute operating instructions 508 to cause the system/apparatus to perform any of the methods described herein. The operating instructions 508 may comprise code (i.e. drivers) relating to the hardware components of the system/apparatus 500, as well as code relating to the basic operation of the system/apparatus 500. Generally speaking, the one or more processors 502 execute one or more instructions of the operating instructions 508, which are stored permanently or semi-permanently in the non-volatile memory 506, using the volatile memory 504 to store temporarily data generated during execution of said operating instructions 508.

Implementations of the methods described herein may be realised as in digital electronic circuitry, integrated circuitry, specially designed ASICs (application specific integrated circuits), computer hardware, firmware, software, and/or combinations thereof. These may include computer program products (such as software stored on e.g. magnetic discs, optical disks, memory, Programmable Logic Devices) comprising computer readable instructions that, when executed by a computer, such as that described in relation to FIG. 5, cause the computer to perform one or more of the methods described herein.

Any system feature as described herein may also be provided as a method feature, and vice versa. As used herein, means plus function features may be expressed alternatively in terms of their corresponding structure. In particular, method aspects may be applied to system aspects, and vice versa.

Furthermore, any, some and/or all features in one aspect can be applied to any, some and/or all features in any other aspect, in any appropriate combination. It should also be appreciated that particular combinations of the various features described and defined in any aspects of the disclosure can be implemented and/or supplied and/or used independently.

Although several embodiments have been shown and described, it would be appreciated by those skilled in the art that changes may be made in these embodiments without departing from the principles of this disclosure, the scope of which is defined in the claims and their equivalents.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetrade-canoyl)-des(B30) human insulin (insulin detemir, Levemir®), B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-112600 (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the embodiments of the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A computer-implemented method of generating a molecule, the computer-implemented method comprising:

sequentially processing, by a memory network, each token in a token string representation of a molecular scaffold to generate a molecule by processing a first token in the token string representation and subsequently processing each remaining token in the token string representation in sequence, wherein the first token and each remaining token in the token string representation together comprise a plurality of tokens representing predefined structures of the molecular scaffold and one or more tokens representing open positions of the molecular scaffold, and wherein the memory network encodes a sequential probability distribution on each token in the token string representation using an internal state of the memory network, wherein sequentially processing each token in the token string representation of the molecular scaffold comprises:

determining whether a current token being processed is a token representing an open position of the molecule; and if the current token does not represent an open position of the molecular scaffold, reading the current token into the memory network and updating the internal state of the memory network based on the current token, or if the current token does represent an open position of the molecular scaffold, sampling one or more candidate tokens for the open position based on a current internal state of the memory network until a termination condition is satisfied and updating the internal state of the memory network after each sampled token based on the sampled token such that multiple open positions of the molecular scaffold are completed in one pass through a sequence of the plurality of tokens; and outputting, from the memory network, a token string representation of the generated molecule.

2. The computer-implemented method of claim 1, wherein the one or more tokens representing open positions respectively represent one or more different open position types, and wherein the termination condition for sampling one or both of the one or more candidate tokens at an open position and tokens available for sampling at an open position are dependent on an open position type of the open position.

3. The computer-implemented method of claim 1, further comprising resuming sequential processing of the token string representation of the molecular scaffold after the termination condition for an open position is satisfied.

4. The computer-implemented method of claim 1, wherein at least one of the tokens representing an open position of the molecular scaffold represents an open branch of the molecular scaffold.

5. The computer-implemented method of claim 4, wherein a set of allowed tokens for the token string representation comprises a branch-opening token and a branch-closing token, and wherein sampling one or more candidate tokens at an open position representing the open branch of the molecular scaffold comprises sampling candidate tokens until a number of sampled branch-closing tokens is equal to a number of branch-opening tokens in the candidate tokens.

6. The computer-implemented method of claim 4, wherein one or more tokens of the open branch are constrained.

7. The computer-implemented method of claim 4, wherein the open branch is constrained to be a linear fragment.

8. The computer-implemented method of claim 1, wherein at least one of the tokens representing an open position of the molecular scaffold represents an open linker within the molecular scaffold.

9. The computer-implemented method of claim 8, wherein sampling one or more candidate tokens at an open position representing an open linker of the molecular scaffold comprises:

determining a threshold number of candidate tokens to be sampled based on a pre-defined probability distribution; and sampling candidate tokens until a number of sampled tokens reaches the threshold number of candidate tokens.

10. The computer-implemented method of claim 9, wherein a set of allowed tokens for the token string representation comprises one or both of a branch-opening token and a branch-closing token and one or more cycle opening and cycle closing tokens, and wherein sampling one or more candidate tokens at an open position representing an open linker of the molecular scaffold further comprises continuing to sample candidate tokens beyond the threshold number of sampled tokens until all branches are closed and all cycles are closed.

11. The computer-implemented method of claim 1, wherein the token string representation is a SMILES representation.

12. The computer-implemented method of claim 1, wherein the token string representation comprises a 1-letter or 3-letter amino acid representation.

13. The computer-implemented method of claim 1, further comprising iteratively:

generating one or more molecular structures scoring each molecular structure of the one or more molecular structures using a scoring function representing one or more target properties of a target molecule;

storing the molecular structure as part of a set of potentially biologically or medically active molecules if a threshold condition relating to the scoring function is satisfied; and fine tuning parameters of the memory network based on the score for the molecular structure.

14. The computer-implemented method of claim 13, further comprising synthesizing the molecule based on the molecular structure.

15. The computer-implemented method of claim 13, wherein the computer-implemented method comprises a lead optimization method.

16. The computer-implemented method of claim 1, wherein the molecule comprises a potentially biologically or medically active molecule.

17. A system comprising one or more processors and a memory, the memory comprising computer-readable instructions that, when executed by the one or more processors, causes the system to perform steps comprising:

sequentially processing, by the memory, each token in a token string representation of a molecular scaffold to generate a molecule by processing a first token in the token string representation and subsequently processing each remaining token in the token string representation in sequence, wherein the first token and each remaining token in the token string representation together comprise a plurality of tokens representing predefined structures of the molecular scaffold and one or more tokens representing open positions of the molecular scaffold, and wherein the memory network encodes a sequential probability distribution on each token in the token string representation using an internal state of the memory network, wherein sequentially processing each token in the token string representation of the molecular scaffold comprises:

determining whether a current token being processed is a token representing an open position of the molecule; and if the current token does not represent an open position of the molecular scaffold, reading the current token into the memory network and updating the internal state of the memory network based on the current token, or if the current token does represent an open position of the molecular scaffold, sampling one or more candidate tokens for the open position based on a current internal state of the memory network until a termination condition is satisfied and updating the internal state of the memory network after each sampled token based on the sampled token such that multiple open positions of the molecular scaffold are completed in one pass through a sequence of the plurality of tokens; and outputting, from the memory network, a token string representation of the generated molecule.

18. The system of claim 17, wherein the molecule comprises a potentially biologically or medically active molecule.

19. A drug generated according to a computer-implemented method, the computer-implemented method comprising:

sequentially processing, by a memory network, each token in a token string representation of a molecular scaffold to generate a molecule by processing a first token in the token string representation and subsequently processing each remaining token in the token string representation in sequence, wherein the first token and each remaining token in the token string representation together comprise a plurality of tokens representing predefined structures of the molecular scaffold and one or more tokens representing open positions of the molecular scaffold, and wherein the memory network encodes a sequential probability distribution on each token in the token string representation using an internal state of the memory network, wherein sequentially processing each token in the token string representation of the molecular scaffold comprises:

determining whether a current token being processed is a token representing an open position of the molecule; and if the current token does not represent an open position of the molecular scaffold, reading the current token into the memory network and updating the internal state of the memory network based on the current token, or if the current token does represent an open position of the molecular scaffold, sampling one or more candidate tokens for the open position based on a current internal state of the memory network until a termination condition is satisfied and updating the internal state of the memory network after each sampled token based on the sampled token such that multiple open positions of the molecular scaffold are completed in one pass through a sequence of the plurality of tokens; and outputting, from the memory network, a token string representation of the generated molecule.

20. The drug of claim 19, wherein the molecule comprises a biologically or medically active molecule.

* * * * *